US009208553B2

(12) United States Patent
Cao et al.

(10) Patent No.: US 9,208,553 B2
(45) Date of Patent: *Dec. 8, 2015

(54) IMAGE SYNCHRONIZATION OF SCANNING WAFER INSPECTION SYSTEM

(71) Applicant: KLA-Tencor Corporation, Milpitas, CA (US)

(72) Inventors: Kai Cao, Fremont, CA (US); Dennis G. Emge, Naperville, IL (US); Zhiqin Wang, Jersey City, NJ (US); Jamie M. Sullivan, Eugene, OR (US); Wenjian Cai, Sunnyvale, CA (US); Henrik Nielsen, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,372

(22) Filed: Feb. 27, 2015

(65) Prior Publication Data

US 2015/0170357 A1 Jun. 18, 2015

Related U.S. Application Data

(63) Continuation of application No. 13/898,736, filed on May 21, 2013, now Pat. No. 8,995,746.

(60) Provisional application No. 61/800,547, filed on Mar. 15, 2013.

(51) Int. Cl.
*G06K 9/00* (2006.01)
*G06T 7/00* (2006.01)
*G01N 21/95* (2006.01)

(52) U.S. Cl.
CPC .......... *G06T 7/0004* (2013.01); *G01N 21/9501* (2013.01)

(58) Field of Classification Search
None
See application file for complete search history.

(56) References Cited

U.S. PATENT DOCUMENTS 6,775,051 B2 8/2004 Sullivan et al.
2002/0088940 A1* 7/2002 Watanabe et al. ............. 250/310

(Continued)

FOREIGN PATENT DOCUMENTS

JP 2011059570 A 3/2011
KR 20070091668 A 9/2007

OTHER PUBLICATIONS

"U.S. Appl. No. 13/898,736, Notice of Allowance mailed Nov. 28, 2014", 12 pgs.

(Continued)

*Primary Examiner* — Amara Abdi
(74) *Attorney, Agent, or Firm* — Kwan & Olynick LLP

(57) ABSTRACT

An inspection system comprises a beam generator module for deflecting spots across scan portions of a specimen. The system also includes detection channels for sensing light emanating from a specimen in response to an incident beam directed towards such specimen and generating a detected image for each scan portion. The system comprises a synchronization system comprising clock generator modules for generating timing signals for deflectors of the beam generator module to scan the spots across the scan portions at a specified frequency and each of the detection channels to generate the corresponding detected image at a specified sampling rate. The timing signals are generated based on a common system clock and cause the deflectors to scan the spots and the detection channels to generate a detected image at a synchronized timing so as to minimize jitter between the scan portions in the response image.

23 Claims, 8 Drawing Sheets

(56) References Cited

U.S. PATENT DOCUMENTS

| | | | |
|---|---|---|---|
| 2002/0097393 A1* | 7/2002 | Nikoonahad et al. | 356/237.2 |
| 2005/0230618 A1 | 10/2005 | Onishi et al. | |
| 2008/0013076 A1* | 1/2008 | Matsui | 356/73 |
| 2012/0196454 A1 | 8/2012 | Shah et al. | |
| 2012/0218623 A1* | 8/2012 | Sandstrom | 359/305 |
| 2013/0050687 A1* | 2/2013 | Aizenberg | 356/128 |
| 2013/0050689 A1 | 2/2013 | Reich et al. | |
| 2013/0169957 A1* | 7/2013 | Wolf et al. | 356/237.1 |
| 2014/0270471 A1 | 9/2014 | Cao et al. | |

OTHER PUBLICATIONS

"International Application Serial No. PCT/US2014/026144, Search Report and Written Opinion mailed Jun. 24, 2014", 10 pgs.

* cited by examiner

IMAGE SYNCHRONIZATION OF SCANNING WAFER INSPECTION SYSTEM

CROSS-REFERENCE TO RELATED APPLICATIONS

This application is a continuation of and claims the benefit under 35 U.S.C. §120 of U.S. application Ser. No. 13/898,736, filed May 21, 2013, titled "IMAGE SYNCHRONIZATION OF SCANNING WAFER INSPECTION SYSTEM", by Kai Cao et al., which claims priority under 35 U.S.C. §119 of prior U.S. Provisional Application No. 61/800,547, filed Mar. 15, 2013, titled "IMAGE SYNCHRONIZATION OF SCANNING WAFER INSPECTION SYSTEM" by Kai Cao, et al. Both applications are herein incorporated by reference in their entireties for all purposes.

TECHNICAL FIELD OF THE INVENTION

The present invention relates generally to inspection and metrology systems. More specifically, it relates to scanning type systems for inspecting and measuring semiconductor wafers and other types of patterned samples.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. Each device needs to be fault free prior to shipment to the end users or customers.

Various inspection systems are used within the semiconductor industry to detect defects on a semiconductor reticle or wafer. Some conventional optical inspection tools locate defects on patterned wafers by scanning the surface of the wafer with a tightly focused laser spot and measuring the amount of light scattered by the illuminated spot on the wafer. Dissimilarities in the scattering intensity between similar locations in adjacent dies are recorded as potential defect sites.

Some conventional scanning systems include an illumination system one or more incident beam sources for deflecting one or more beams across the wafer. The scanning system may specifically include an acousto-optic deflectors (AOD's) and a mechanism for controlling the AOD's deflection characteristics. For instance, a clock may be used to generate a "chirp" signal input to each AOD.

It would be beneficial to provide improved inspection systems having deflectors, such as AOD's.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting or measuring a specimen using an inspection system comprising a pre-scanner acousto-optic deflector (AOD), a chirp AOD, and a plurality of detection channels is disclosed. A common trigger clock is used to generate a chirp clock and input a chirp frequency ramp signal into the chirp AOD based on the generated chirp clock. In response to the chirp frequency ramp signal input to the chirp AOD, a chirp packet is propagated through the chirp AOD. The common trigger clock is also used to generate a pre-scanner clock and input a pre-scanner frequency ramp signal into the pre-scanner AOD based on the generated pre-scanner clock, and the pre-scanner AOD receives and deflects an incident beam onto the propagating chirp packet in the chirp AOD, causing one or more spots to be scanned in a plurality of lines across the specimen. The common trigger clock is also used to generate an acquisition clock for each detection channel and input a sampling frequency signal into such detection channel based on the generated acquisition clock for such detection channel. At each detection channel, light is detected from the specimen in response to one or more spots scanned across the specimen and a detected image is detected that has a sampling rate that is based on the sampling frequency signal.

In a specific implementation, the chirp clock has a same period as the common trigger clock. In a further aspect, the chirp frequency ramp signal is triggered off an edge of the chirp clock. In yet a further aspect, the chirp frequency ramp signal has a period that is equal to half a period of the chirp clock and the common trigger clock. In another embodiment, a period of the common trigger clock is selected based on a desired size of each spot. In a further aspect, the period of the common trigger clock is selected so that a period of the resulting chirp frequency ramp signal matches a relative stage movement that causes scanning of the one or more spots to move from a first set of one or more scan lines to a second set of one or more scan lines. In yet another example, the pre-scanner clock is delayed from the chirp clock by a time duration equal to a fill time of the chirp AOD minus a fill time of the pre-scanner AOD.

In another embodiment, the inspection system further comprises a diffractive element or mirror system for receiving a single spot deflected from the chirp AOD and causing a plurality of spots to be scanned in a plurality of lines across the specimen. In another embodiment, each image acquisition clock of each detection channel is triggered after a fill time of the chirp AOD. In a further aspect, a frequency of each acquisition clock is adjusted based on a predefined distortion amount of the corresponding detection channel. In yet a further aspect, the frequency of each acquisition clock is adjusted per each spot of the corresponding detection channel, wherein such adjustment is based on a predefined distortion amount for such spot. In another feature, the acquisition clock and associated sampling frequency signal for each detection channel is controlled so that sampling a plurality of locations on the specimen substantially accurately follows the scanning of the one or more spots at they traverse along the plurality of lines. In yet another feature, the acquisition clock and associated sampling frequency signal for each spot of each detection channel is controlled so that sampling a plurality of locations on the specimen follows the scanning of such spot at it scans along a plurality of lines. In another embodiment, the method includes analyzing the detected images generated by the detection channels to detect defects on such specimen.

In an alternative embodiment, the invention pertains to a system for inspecting or measuring a specimen. This system comprises a beam generator module for deflecting one or more spots across a plurality of scan portions of the specimen, and the scan portions include one or more first scan portions and one or more next scan portions that are scanned after the one or more first scan portions. The system also includes one or more detection channels for sensing light emanating from a specimen in response to an incident beam directed towards such specimen and generating a detected image for each scan portion as the incident beam is scanned over such scan portions. The system further comprises a synchronization system comprising a plurality of clock generator modules for generating a plurality of timing signals for one or more deflectors of the beam generator module to scan the one or more spots across the scan portions at a specified frequency and for each of the detection channels to generate the corresponding detected image at a specified sampling rate. The timing signals are generated based on a common system clock and cause the one or more deflectors to scan the one or more spots and the detection channels to generate a detected image at a synchronized timing so as to minimize jitter between the scan portions in the response image In a specific embodiment, the clock generator modules comprise a plurality of direct digital synthesizers (DDS's) for generating a scanning clock for each of the one or more deflectors and generating a sampling rate for each detection channel, wherein the synchronization system further comprises a synchronization signal clock driver for determining a timing for each DDS module. In specific implementations, the beam generator module comprises a pre-scanner AOD and a chirp AOD, and the synchronization system is configured to perform one or more of the above-described operations.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

In general, certain embodiments of the present invention employ mechanisms for controlling the timing of an inspection system's illumination scan rate and image (or signal) acquisition sampling rate. These timing mechanisms may be integrated into any suitable type of inspection system that has an illumination system for scanning one or more spots across a sample and one or more image acquisition channels for generating one or more detected signals or images based on detected light emitted from the sample in response to the one or more illumination spots that are scanning across such sample. The inspection system may include any suitable number and type of deflector and detection modules or channels. In a specific optical scanning inspection tool, an acousto-optic deflector (AOD) based scanning system is synchronized with the image acquisition system, resulting in an accurate image with minimum line jitter. The optics distortion also can be corrected by changing the frequency of image acquisition's ADC clocks with direct digital synthesizer (DDS) technology. Timing mechanism embodiments of the present invention may be applied to other types of deflector types, such as galvanometer-driven mirrors, etc.

Prior to describing specific timing mechanisms, a general inspection system will first be described. Although this system is described as having an illumination system for generating a single illumination spot and three detection channels, timing mechanisms of the present invention may be integrated with a system that generates multiple scanning spots and/or has multiple detection channels for detecting light from any suitable angle and any number of scanning spots.

Figure 1:
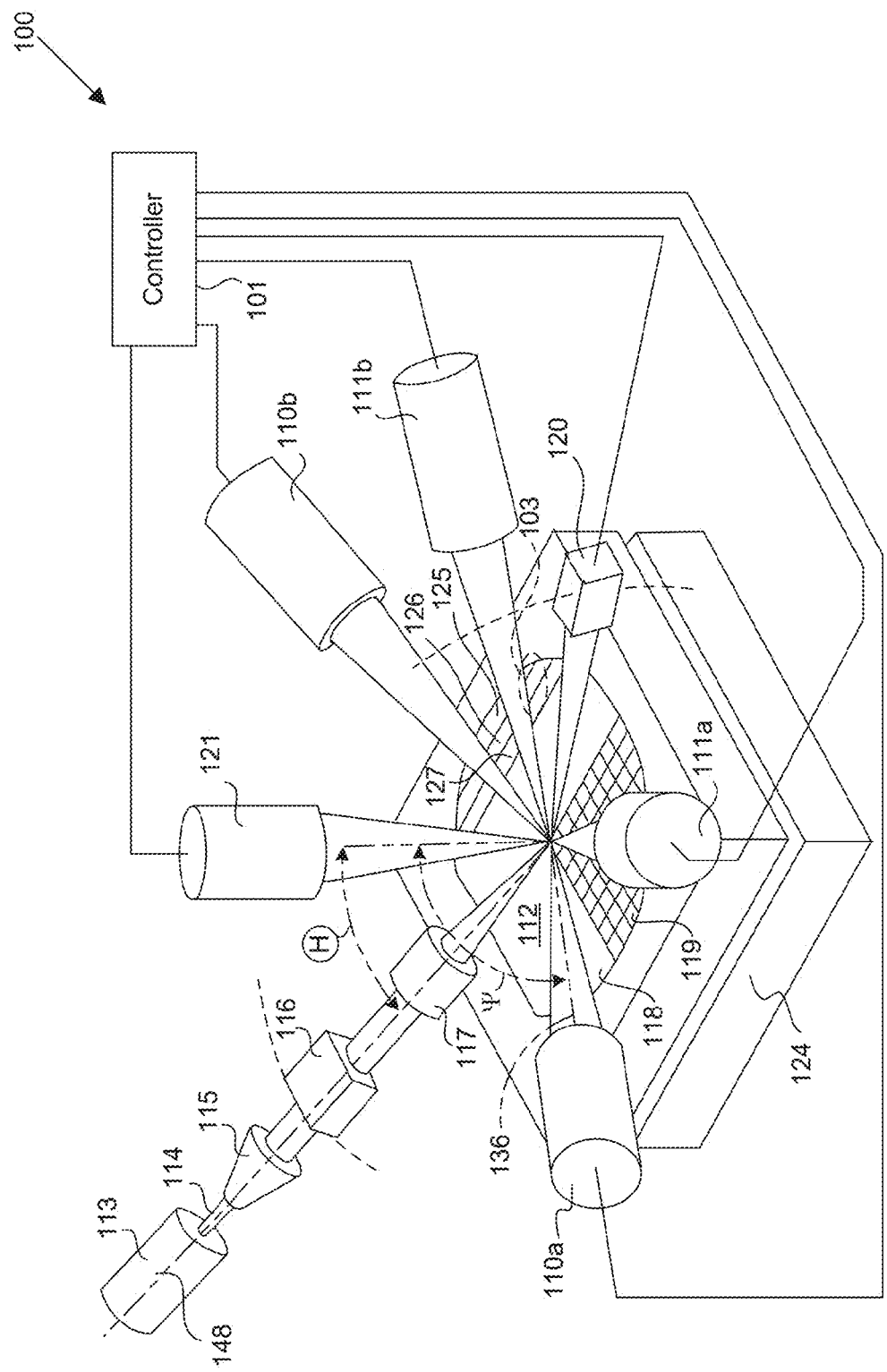
FIG. 1 is a diagrammatic representation of an example optical system in which embodiments of the present invention may be implemented.

FIG. 1 is a diagrammatic representation of an example optical system 100 in which embodiments of the present invention may be implemented. The optical system 100 includes any suitable number of detectors or collection channels for detecting light emitted from a sample, such as a semiconductor wafer surface. The detectors or collection channels may be arranged in any suitable position, and such arrangement depends on the particular requirements of the inspection application. The illustrated embodiment uses two groups of two collector channels, 110a-b and 111a-b, disposed symmetrically about the wafer surface 112 so that each collector channel within a pair is located at the same azimuthal angle on opposite sides of the scan line. These azimuthal collector channels detect scattered light. The output from the collector channels may then be sent to controller 101 for data analysis and/or image generation. The data from the channels may be compared by performing various algorithms and logical operations, e.g., OR, AND and XOR.

The optical system also includes a beam generator (e.g., components 113, 115, 116, and 117) for generating an incident beam and directing it towards a sample. As shown in FIG. 1, a light source 113, typically a laser, emits a beam 114. Beam 114 is directed towards pre-deflector optics 115, which may include a half wave-plate, a spatial filter and several cylindrical lenses, in order to produce an elliptical beam with a desired polarization that is compatible with the deflector module 116. The pre-deflector optics 115 may be configured to expand the beam 114 to obtain the appropriate numerical aperture. The post-deflector optics 117 may include several cylindrical lenses and an air slit. Finally, the beam 114 may be brought into focus on the wafer surface 112 and scanned along a particular direction, in the plane of the wafer surface 112, perpendicular to the optical axis of the beam 114. The type of deflector employed in the apparatus is application dependent. In one embodiment, deflector 116 includes one or more Acousto-Optic Deflectors (AODs).

The wafer surface 112 may be smooth 118 or patterned 119. In addition to the collector channels 110a-b and 111a-b, described above, detector channels may be provided which include a reflectivity/auto-position channel 120, and a normal collector channel 121. each of which are discussed more fully below.

The wavelength of the beam 114 depends on the particular requirements of the application. In the illustrated embodiment, the beam 114 has a wavelength of about 488 nm. Beam 114 can be produced by any suitable light source, such as an Argon ion laser. The optical axis 148 of the beam 114 is directed onto the wafer surface 112 at an angle θ. This angle θ is preferably in the range of 55-85 degrees with respect to the normal to the wafer surface 112, depending on the particular application. The scanning mechanism includes the deflector 116 and the translation or sample stage 124, upon which the wafer or sample rests. The position of the wafer on the stage 124 is maintained in any convenient manner, e.g., via vacuum suction. The stage 124 can move to partition the surface 112 into striped regions or scan lines, shown as 125, 126 and 127 with the deflector 116 moving the beam across the width of the striped regions.

Each illumination optics column may be moved with respect to the stage and/or the stage moved relative to each collection channel, including one or more detectors or cameras, by any suitable mechanism so as to scan the sample. For example, a motor mechanism may be utilized to move the stage or any other component of the system. Each motor mechanism may be formed from a screw drive and stepper motor, linear drive with feedback position, or band actuator and stepper motor, by way of examples.

Light scattered from the wafer surface 112 can be detected by a plurality of detectors, including collector channels 110a-b and 111a-b. The collector channels can be arranged to collect light over a fixed solid angle, dependent upon, inter alia, the elevational and azimuthal angle of the channel. The optical axis of each collection channel is positioned at an angle of elevation ψ in the range of 0 to 90 degrees with respect to the normal to the surface 112. Collector channels 110a and 110b can be symmetrically positioned at the same azimuthal angle with respect to beam 114, on opposite sides of the scan line. Collector channels 110a and 110b are positioned, with respect to the beam 114, at an azimuthal angle ψ$_1$ in the range of about 75 to about 105 degrees to collect laterally scattered light. Laterally scattered light is defined as light scattered at azimuthal angles in the range of about 75 to about 105 degrees, with respect to beam 114. Similar to collector channels 110a and 110b, channels 111a and 111b can be positioned on opposite sides of the scan line at the same azimuthal angle. However, the azimuthal angles ψ$_2$ of channels 111a and 111b are in the range of 30 to 60 degrees, to collect forwardly scattered light. Forwardly scattered light is defined as light scattered at azimuthal angles in the range of 30 to 60 degrees. Those of ordinary skill in the art will readily recognize that the number and location of the collector channels and/or their collection solid angle may be changed in various alternative embodiments without departing from the scope of the invention.

The bright field reflectivity/autoposition channel 120, can be positioned in front of the beam 114 to collect specularly reflected light. The bright field signal derived from this channel carries information concerning the pattern, local variations in reflectivity and height. This channel is sensitive to detecting various defects on a surface. For example, the bright field signal is sensitive to representing film thickness variations, discoloration, stains and local changes in dielectric constant. The bright field signal is also used to produce an error height signal, corresponding to a variation in wafer height, which is fed to a z-stage to adjust the height accordingly. Finally, the bright field signal can be used to construct a reflectivity map of the surface. In one embodiment, this channel is basically an unfolded Type I confocal microscope operating in reflection mode. It is considered unfolded because the illuminating beam and reflected beams, here, are not collinear, as compared with a typical reflection confocal microscope in which the illuminating and reflected beams are collinear.

The normal collector channel collects light over a fixed solid angle over a region which is approximately perpendicular to the plane of the wafer. Other than the collection solid angle, the normal collector implementation may be similar to the other collector channels 110ab and 111ab. The normal collector may be used to collect scattered light from the intentional patterns on the wafer, as well as to detect defects which scatter light in an upwards direction. Signals collected from the intentional patterns may be used to facilitate the alignment and registration of the wafer pattern to the coordinate system of the mechanical stage in the instrument.

One or more of the collector channels may include mechanism for increasing the dynamic range of detected output signals. Preferably, these mechanisms for increasing dynamic range are provided within collector channels 110ab, 111ab and 121. In general terms, a high dynamic range collector includes a light sensor, such as a photomultiplier tube (PMT), for generating a signal from detected photons and an analog to digital converter (ADC) for converting the light signal to a digital light signal. Suitable PMT's include a circular cage type PMT, metal-channel photomultiplier, etc. Of course, other suitable mechanism may be used for sensing light and converting an analog signal into a digital signal.

The grazing angle of the beam 114 may produce an elliptical spot on the wafer surface 112, having a major axis perpendicular to the scan line. The deflectors 116 scan the spot across a short scan line equal in length to the length of scan line 125 to produce reflected and scattered light. The spot may be scanned in a first direction, as the stage 124 moves the wafer perpendicular to the scan line. This results in the spot moving along scan line 125.

In one implementation, the illumination beam 114 is raster scanned along multiple scan lines 125, 126, and 127 one at a time. For example, a first scan line 125 has an effective start location and the spot moves from left to right along such first scan line until the beam reaches the border of the first scan line. Upon reaching the border of scan line 125, the spot moves relative to the stage 124 perpendicular to the scan direction and the spot then has a new start position for a new second scan line 126. The spot then moves along this second scan line 126 parallel to the first scan line. The deflector 116 continues to scan the spot in this fashion along the entire length of the second scan line 126. Upon completion of the second scan line 126, the stage 124 moves relative to the wafer to permit the scanning of the adjacent third scan line 127. The spot moves along the third scan line 127 in a direction opposite to that when scanning the second scan line 126, thereby forming a serpentine scan.

Figure 2:
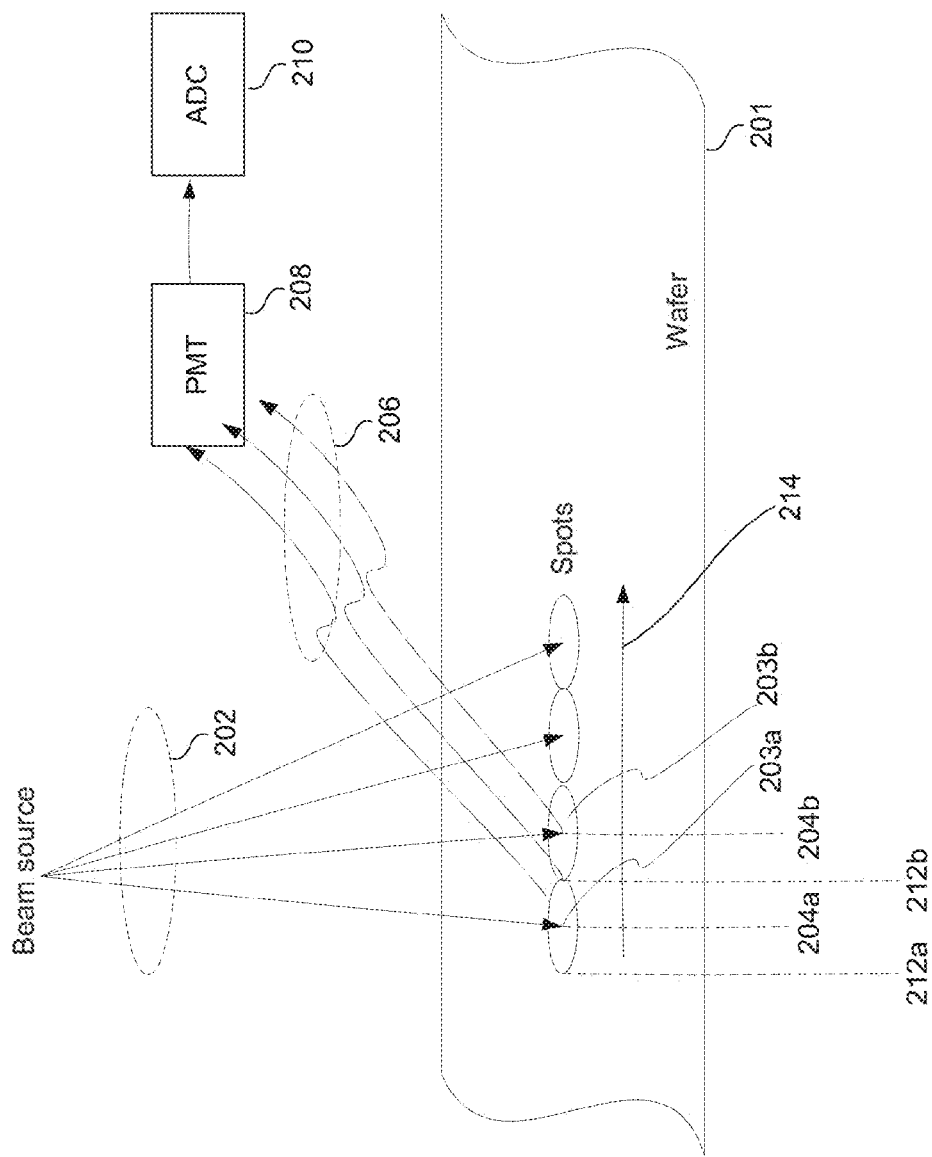
FIG. 2 is a diagrammatic representation of scanning an illumination spot across a sample and detecting light that is emitted from such sample in response to such illumination spot.

FIG. 2 is a diagrammatic representation of scanning an illumination spot across a scan line of wafer 201 and detecting light that is emitted from such wafer in response to such illumination spot. As shown, illumination beam 202 is scanned in direction 214 across wafer 201. As such beam 202 moves, illumination spot is scanned across a scan line of such wafer. For instance, the scanning illumination beam 202 causes spot 203a at a first time to be formed at position 204a and then causes spot 203b at a second subsequent time to be formed at position 204b on the specimen 201. Thus, a spot moves in direction 214.

As each illumination spot is moved along a scan line, corresponding light 206 may be detected by a sensor, such as photo-multiplier tube (PMT) 208. The PMT generates and outputs a signal based on the detected light to an analog-to-digital (ADC) 210. As the PMT detects and continuously outputs a detected signal corresponding to different wafer positions along the scan line, the ADC samples at a specified sampling rate the detected signal and produces a digital representation of each detected signal sample interval. That is, the ADC 210 samples and converts portions of the detected signal at particular time intervals. Each sampling time interval corresponds to particular positions on the wafer. The digital representation may then be used to generate an image.

To prevent line jitter occurring in an image produced from the sampled signal, the timing of the ADC 210 is controlled such that the sampled portions of the detected signal correspond to each spot position on the wafer 201. For instance, a first sampling time interval corresponds to first spot 203a having a center position 204a and edge positions 212a and 212b. The second sampling time would then correspond to a second spot 203b at center position 204b. Thus, the ADC's sampling time is selected to follow the timing of the spot as it moves across each scan line. The ADC also samples each end pixel or spot of each scan line at the correct position on the wafer so that the resulting image lines are not skewed with respect to each other. For instance, the sampling rate input to the ADC may be selected to prevent the image sampling of each scan line from starting at an early or delayed position that corresponds to an edge of the first spot of a scan line (e.g., 212a or 112b), but rather starting at the center position (e.g., 204a) of the first pixel of the scan line. The sampling may result in different spot and pixel relationships. For instance, a spot can correspond to one pixel or multiple pixels.

In slower scan systems, precise synchronization between the sampling timing of the image acquisition and the scan timing may not be a significant issue. For instance, a 100 MHz system may correspond to a 10 ns width for each pixel, and a sampling error of 2 ns may correspond to only ⅕ of a pixel. However, a faster system, such as a 5 GHz, may correspond to a 200 ps pixel width, and a 2 ns sampling error would correspond to a 10 pixel error, which would cause the acquired image to appear significantly skewed. Accordingly, certain embodiments of the present invention provide timing control such that the image acquisition system operates at an imaging rate that is synchronized with the scan rate. The resulting image is not skewed.

Figure 3:
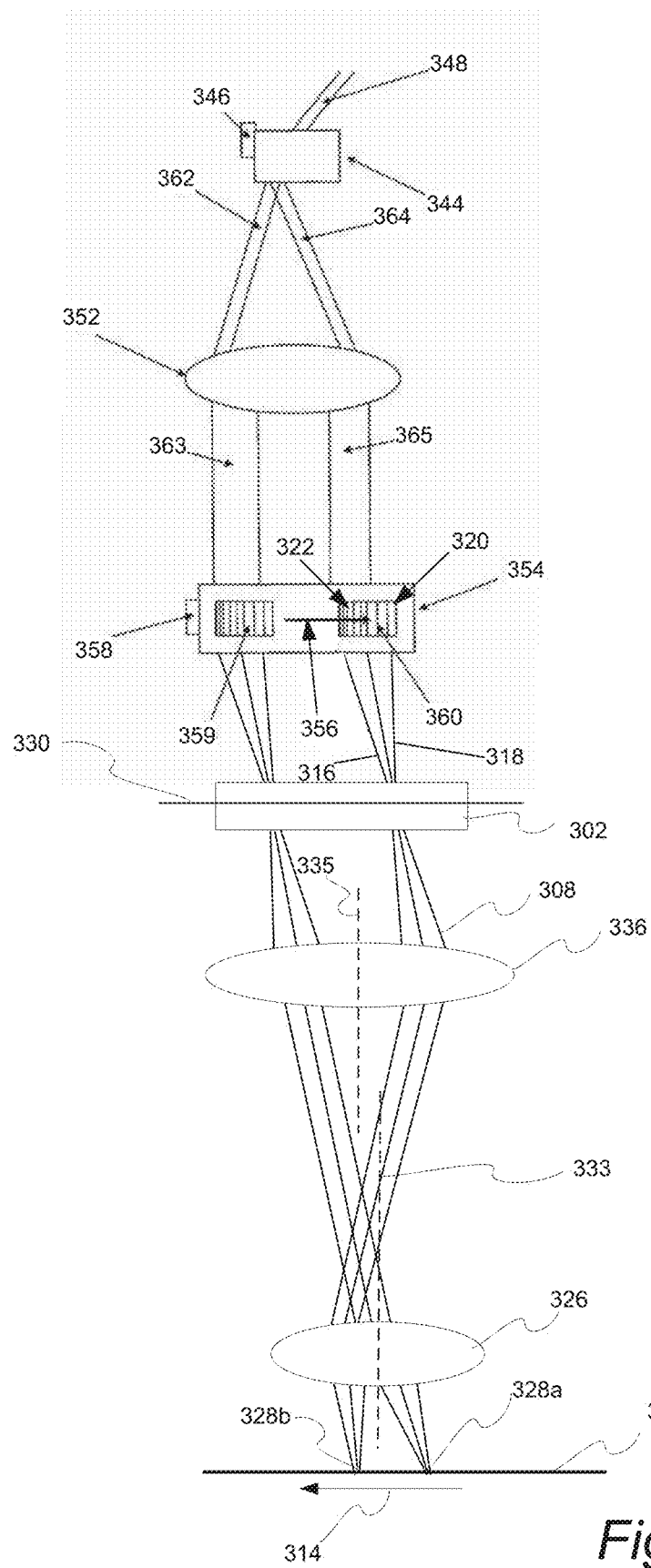
FIG. 3 is a diagrammatic representation of illumination optics of an inspection system that includes a pre-scanner acousto-optic deflector (AOD) and a chirp AOD.

In some inspection systems, a pre-scanner AOD and a chirp AOD are utilized to scan a spot across each line on the sample under test. FIG. 3 is a diagrammatic representation of illumination optics of an inspection system that includes a pre-scanner acousto-optic deflector (AOD) 344 and a chirp AOD 354. The pre-scanner AOD 344 and chirp AOD 354 may be made of a solid medium that includes, but is not limited to, a crystal material such as $TeO_2$, quartz, fused silica, sapphire, another glassy material, or any other appropriate material known in the art.

A sound transducer 346 may be coupled with a solid medium surface of the pre-scanner AOD 344. Transducer 346 may be configured to generate a drive signal which fills pre-scanner AOD 344 with a sound wave whose frequency varies slowly compared to the propagation time of the sound wave through pre-scanner AOD 344. By varying the frequency of the sound wave in pre-scanner AOD 344, the deflected beam may be scanned from location 362 to location 364.

The system may also include one or more lens 352. Lens 352 may be configured to expand the beam and convert the small angular scan from pre-scanner AOD 344 into a long linear scan at chirp AOD 354. For instance, lens 352 receives a beam at a first position 362 and transmits beam 363. Likewise, lens 352 receives a beam at a last position 364 and transmits beam 365. The lens 352 may also be configured to manipulate the received beam in any number and type of manners. For example, the lens may include a telescope, a relay lens, a focusing lens, an objective lens, a mirror, or any other appropriate optical component known in the art.

Chirp AOD 354 may be operated in chirp mode. Transducer 358 attached or coupled to chirp AOD 354 may be configured to generate a drive signal, which produces a chirp packet that propagates over a width of chirp AOD 354 from position 359 to position 360. The chirp packet generally takes a finite time to form, determined by the desired width of the chirp packet and the acoustic velocity in the AOD. This chirp packet creation time may be referred to herein as a "fill time."

A chirp packet propagating through chirp AOD 354 may be configured to function as a traveling lens to focus the scanning beam into a spot. The width of a chirp packet may be approximately equal to the size of the received light beams, e.g., 363 and 365, which is much less than the width of chirp AOD 354. Alternatively, the chirp AOD 354 may be caused to contain multiple chirp packets at the same time. Each chirp packet may be substantially shorter than the width of the AOD.

A chirp packet propagating through an AOD's solid medium may have a frequency in the ultrasonic range. The chirp packet propagating through such solid medium may alter a property of the solid medium, such as a lattice structure of the crystal or a refractive index. In this manner, a light beam incident on the solid medium of the AOD may propagate through the solid medium and may be diffracted by a portion of the crystal lattice altered by the ultrasonic chirp packet as it propagates through the crystal. As a result, a portion of light exiting an AOD's solid medium may include a deflected beam. A portion of light exiting the solid medium of an AOD, however, may also include one or more substantially undeflected beams. A chirp packet may contain multiple frequencies that change linearly from the start of the packet to the end of the chirp packet commonly referred to as a "frequency ramp."

An angle at which an incident beam may be deflected by an AOD may depend only upon relative wavelengths of light and ultrasound waves inside the AOD. In this manner, an angle of deflection of a beam exiting an AOD may be determined and may be controlled by a wavelength of light incident upon the AOD and a wavelength of an ultrasonic sound wave induced inside the solid medium of the AOD.

For the case of the chirp mode where the drive frequency changes linearly over a chirp packet, the incident beam is diffracted at different angles proportional to the frequency in the chirp packet. By ramping the frequencies from low to high and as illustrated in FIG. 3, a particular portion 322 of the chirp packet 360 may have a higher frequency than another portion 320 of the same chirp packet 360. Because portion 322 has a higher frequency, it diffracts a portion of incident light beam 365 through a steeper angle as shown by diffracted beam 316. Because portion 320 has a relatively lower frequency, it diffracts a portion of incident light beam 365 through a more shallow angle as shown by diffracted light beam 318. In this manner, a chirp packet can be used to focus beam in the plane shown as scan line 330.

An AOD configured in a chirp mode may be restricted to having a bandwidth, or a range of frequencies, of less than approximately 1 octave. Such bandwidth limitations may minimize, or may substantially eliminate, secondary beams of light deflected by the AOD from scanning the surface of a specimen at the same time as the primary beam of light deflected by the AOD. Such an AOD configuration, however, will produce chief rays (e.g., 316 and 318) that will not be perpendicular to scan line 330 generated by AOD 354.

A light source (not shown) and pre-scanner AOD may be configured to direct light to illuminate a single chirp packet as it propagates through chirp AOD 354. In other applications, the light source and pre-scanner AOD may be configured to direct light across substantially an entire width of chirp AOD 354. Such a configuration of a light source and AOD may be referred to herein as a "flood mode" configuration. In this manner, light may be directed to first chirp packet and a second chirp packet or any number of chirp packets along a width of the AOD substantially simultaneously.

As chirp packet propagates through chirp AOD 354 away from transducer 358 from position 359 to position 360 in direction 356, the chirp packet may be attenuated in amplitude. Consequently, light focused onto a scan line by the chirp packet at position 359 may be brighter than light focused onto a scan line by a chirp packet at position 360. This non-uniformity in scan line brightness may detrimentally affect the performance of the inspection system or the matching of multiple systems.

In order to compensate for attenuation of a chirp packet as it propagates through chirp AOD 354, the brightness of the beam illuminating the chirp packet may be varied. This may be accomplished by varying the amplitude of the drive signal applied to first pre-scanner AOD 344 by transducer 346. At the start of the beam sweep, pre-scanner AOD 344 may be driven with a lower amplitude signal, to produce a less bright beam 362 which then illuminates chirp packet at position 359 near transducer 358 in chirp AOD 354. At the end of the beam sweep, pre-scanner AOD 344 may be driven with a higher amplitude signal, to produce a brighter beam 364 which then illuminates chirp packet at position 360 at the end of chirp AOD 354. Amplitude modulation of pre-scanner AOD 344 may thereby compensate for attenuation within chirp AOD 354, producing a final scan line with substantially uniform brightness.

The brightness of a scan line produced by a system as described above may be calibrated by scanning a specimen of uniform reflectivity. Light scattered from different positions along the final scan line may be collected and measured. The amplitude of the drive signal applied to the first AOD may then be modulated as needed to produce a scan line of measured uniform brightness at the specimen. This calibration may compensate not only for attenuation in the second AOD, but for any other non-uniformities in the scanning system.

Each illumination column may also include one or more lens for receiving and manipulating the beams, e.g., 316 and 318, from the chirp AOD 354, so as to scan a spot across the specimen 327, e.g., in direction 314. The illumination system may also be configured to generate multiple spots on the sample. As shown, a diffractive element or mirror system 302 may be configured to direct multiple spots to multiple illumination columns (e.g., the illustrated column includes optics elements 336 and 326). The inspection system may also include multiple detection channels for detecting light from different angles or spots.

A single illumination column (e.g., 336 and 326) for scanning a spot across the sample (e.g., from position 328a to 328b in direction 314) is illustrated for simplification. As shown, the illumination column may include relay lens 336. Relay lens 336 may be configured to collimate light focused by AOD 354. Relay lens 336 may include any appropriate lens known in the art. Optical axis 335 of relay lens 336 may be centered on scan line 330 produced by AOD 354. Optical axis 335 may be parallel to the chief rays (non-secondary rays) of AOD 354.

The system may also include objective lens 326. Objective lens 326 may be configured to focus the light collimated by relay lens 336 onto the focal plane, which is parallel to the surface of the sample 327. Objective lens 326 may include any focusing lens known in the art. The optical axis 335 of relay lens 336 may be centered on scan line 330 produced by AOD 354. In addition, optical axis 335 of relay lens 336 may be perpendicular to scan line 330 produced by AOD 354. Optical axis 335 of relay lens 336 may not be substantially parallel to chief ray (non-secondary) produced by AOD 354.

Optical axis 333 of objective lens 326 may be substantially de-centered with respect to optical axis 335 of relay lens 336. Optical axis 333 of objective lens 326 may be substantially parallel to optical axis 335 of relay lens 336. The pupil of the light collimated and formed by relay lens 336, however, may be substantially centered on objective lens 326. In addition, objective lens 326 may be substantially parallel to the focal plane. In this manner, objective lens 326 may be substantially centered on the focal plane. As such, chief ray (non-secondary) deflected by AOD 354 may be relayed by this optical system at a substantially perpendicular angle to the focal plane. Furthermore, the focal plane may be substantially parallel to surface of specimen 327. In this manner, an angle at which the focal plane may be located with respect to the surface of the specimen may be approximately 0 degrees. Therefore, field tilt associated with a chirp mode of an AOD may be corrected by a system in which the optical axis of an objective lens may be offset from the optical axis of a relay lens.

In an alternative embodiment, optical axis 335 of relay lens 336 may be centered on scan line 330 produced by AOD 354. Chief rays produced by AOD 354 may not be substantially parallel to optical axis 338. Optical axis 338 of relay lens 336 may be perpendicular to scan line 330 produced by AOD 354. Relay lens 336 may be configured to collimate light deflected and focused by the AOD as described in above embodiments. As such, in such an embodiment, light collimated by relay lens 336 may not be centered on objective lens 326.

In an additional embodiment, the system may further include optical mechanism, such as a prism assembly or system of mirrors positioned between the relay and the objective lenses. The system of mirrors or prism assembly may be configured to re-center a pupil of the light collimated by relay lens 336 onto objective lens 326.

The illumination system may also include additional optical components (not shown). For example, additional optical components may include, but may not be limited to, beam splitters, quarter wave plates, polarizers such as linear and circular polarizers, rotating polarizers, rotating analyzers, collimators, focusing lenses, mirrors, dichroic mirrors, partially transmissive mirrors, filters such as spectral or polarizing filters, spatial filters, reflectors, and modulators. Each of these additional optical components may be disposed within the system or may be coupled to any of the components of the system as described herein.

Certain embodiments of the present invention include mechanisms for synchronizing the timing of the illumination and image acquisition so as to minimize line jitter in the acquired image. The XY position in the acquired image and scan line is at least partially controlled by timing signals input to the illumination deflectors (e.g., pre-scanner and chirp AOD) and the image acquisition sampling components (e.g., image acquisition ADC's).

Figure 4:
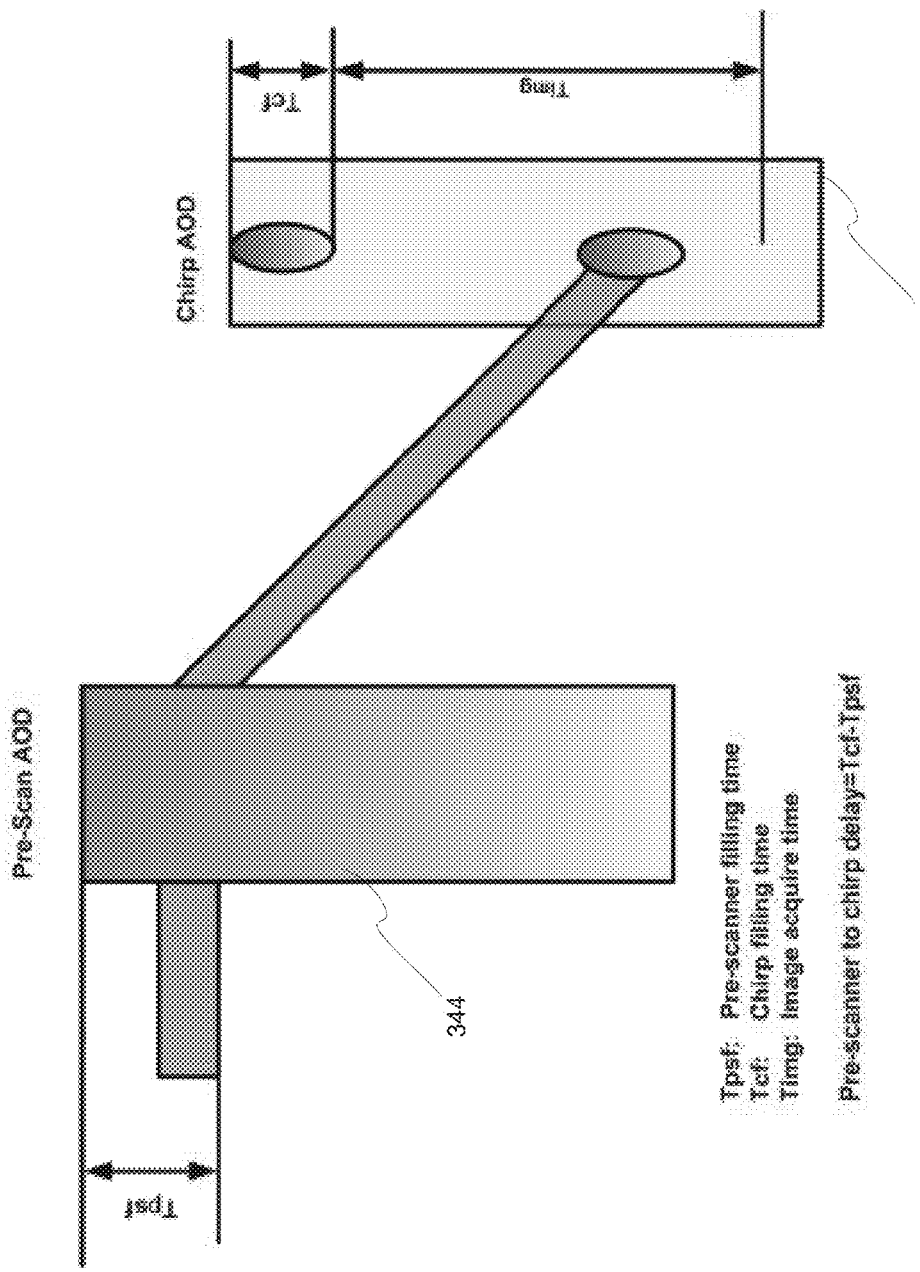
FIG. 4 is a diagrammatic representation of scan timing associated with a pre-scanner AOD and chirp AOD.

The scan timing of a high speed inspection system depends on the deflector timing. FIG. 4 is a diagrammatic representation of scan timing associated with a pre-scanner AOD and chirp AOD. As shown, a pre-scanner fill time ($T_{psf}$) is associated with the pre-scanner 344. The $T_{psf}$ corresponds to the amount of time it takes to fill the pre-scanner AOD with a sound wave. A chirp fill time ($T_{cf}$) is also associated with chirp AOD 354, and this chirp fill time $T_{cf}$ corresponds to the amount of time to fill the chirp AOD with a chirp sound wave (or the time to produce a chirp packet in the chirp AOD). Time $T_{img}$ corresponds to the amount of time the chirp packet takes to scan across the chirp AOD and also corresponds to the time duration during which a spot is scanned across a scan line of the specimen. $T_{img}$ also represents the time during which an image is to be acquired from the specimen in response to the scanned beam.

In certain embodiments, a common clock, such as a fast 2.5 GHz clock, is used to control both the scanning and image acquisition systems of the inspection tool. In a specific example, this fast clock is used to generate 100's of MHz clocks for the AOD and image acquisition system's ADC's. The ADC sampling clocks can be adjusted dynamically to compensate for optical distortion. Optical distortion can be corrected independently for each spot in a multiple scan spot system.

Figure 5:
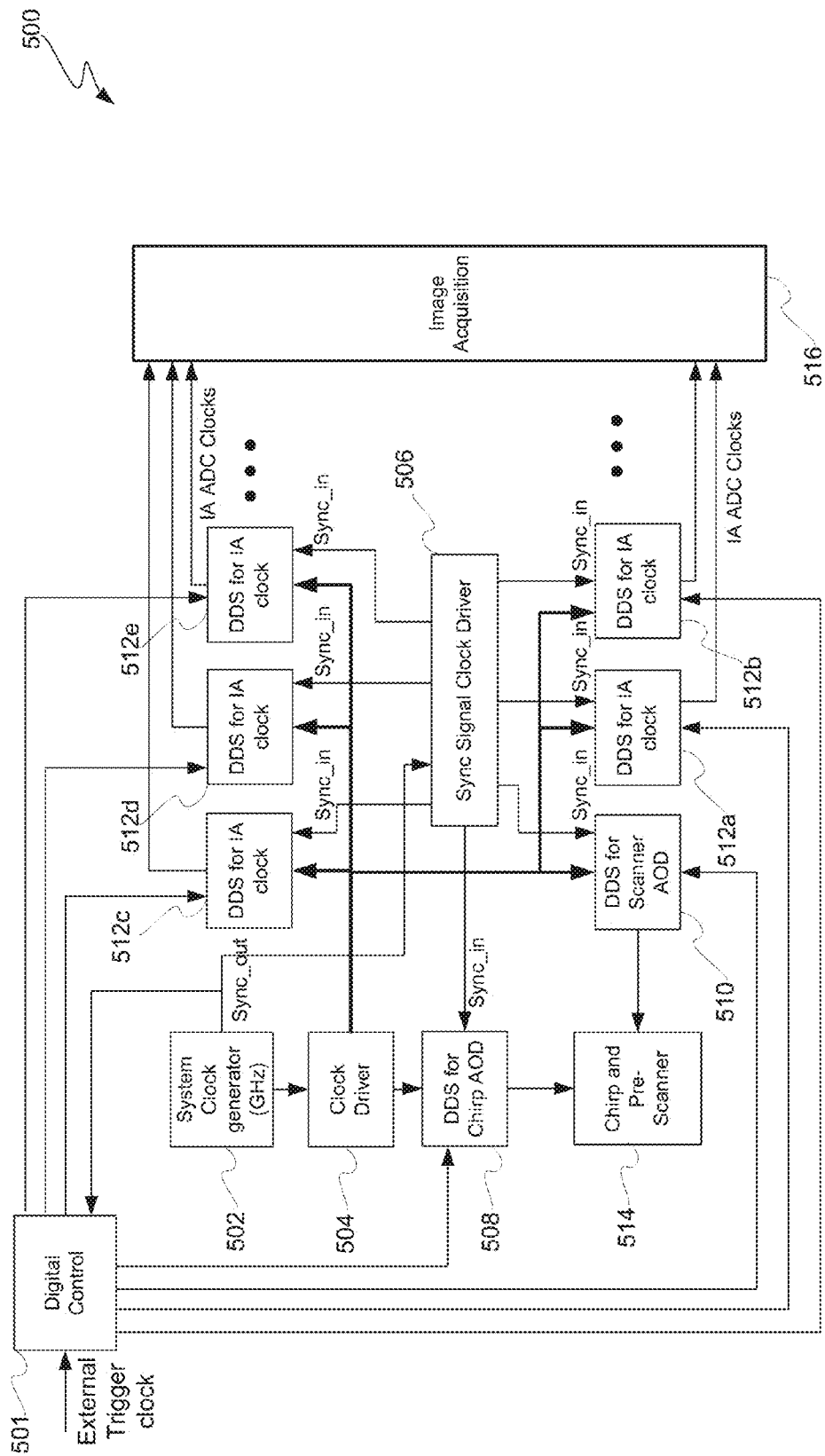
FIG. 5 is a diagrammatic representation of a synchronization system in accordance with one embodiment of the present invention.

FIG. 5 is a diagrammatic representation of a synchronization system 500 in accordance with one embodiment of the present invention. The synchronization system 500 may include any number and type of clock generator modules for generating a clock for each scan and each detection channel. For example, a frequency synthesizer for creating a waveform from a fixed-frequency reference clock may take the form of a direct digital synthesizer (DDS), etc. In the illustrated implementation, the synchronization system 500 includes a DDS for generating a clock at a selected frequency for each scanner and image channel. As shown, DDS 512a-512e are configured to dynamically generate clocks for the multiple detection channels of image acquisition system 516 (e.g., the ADC sampling clocks). The system may also include DDS 510 for generating a clock for the pre-scanner AOD (e.g., of pre-scanner and chirp AOD module 514) and a DDS 508 for generating a clock for the chirp AOD (e.g., of pre-scanner and chirp AOD module 514).

Each DDS module may receive a system clock, which is distributed by clock driver 504 from a system clock generator module 502, and a synchronization signal sync_in signal from a synchronization signal clock driver 506. For instance, the system clock generator module 502 may generate a 2.5 or 5 GHz system clock and the clock driver 504 then distributes this system clock to each DDS.

Each DDS may include any number of components for generating a selected clock for each AOD and ADC. For instance, each DDS may include a numerically (e.g., digitally) controlled frequency register. An input system clock provides a stable time base and provides the clock to the DDS, which produces a discrete-time, quantized version of the desired output with the period controlled by input received into the frequency selection register (from the synchronization signal clock driver 506). Each DDS may also include hardware and/or software for dynamic phase and dynamic frequency control.

Figure 7:
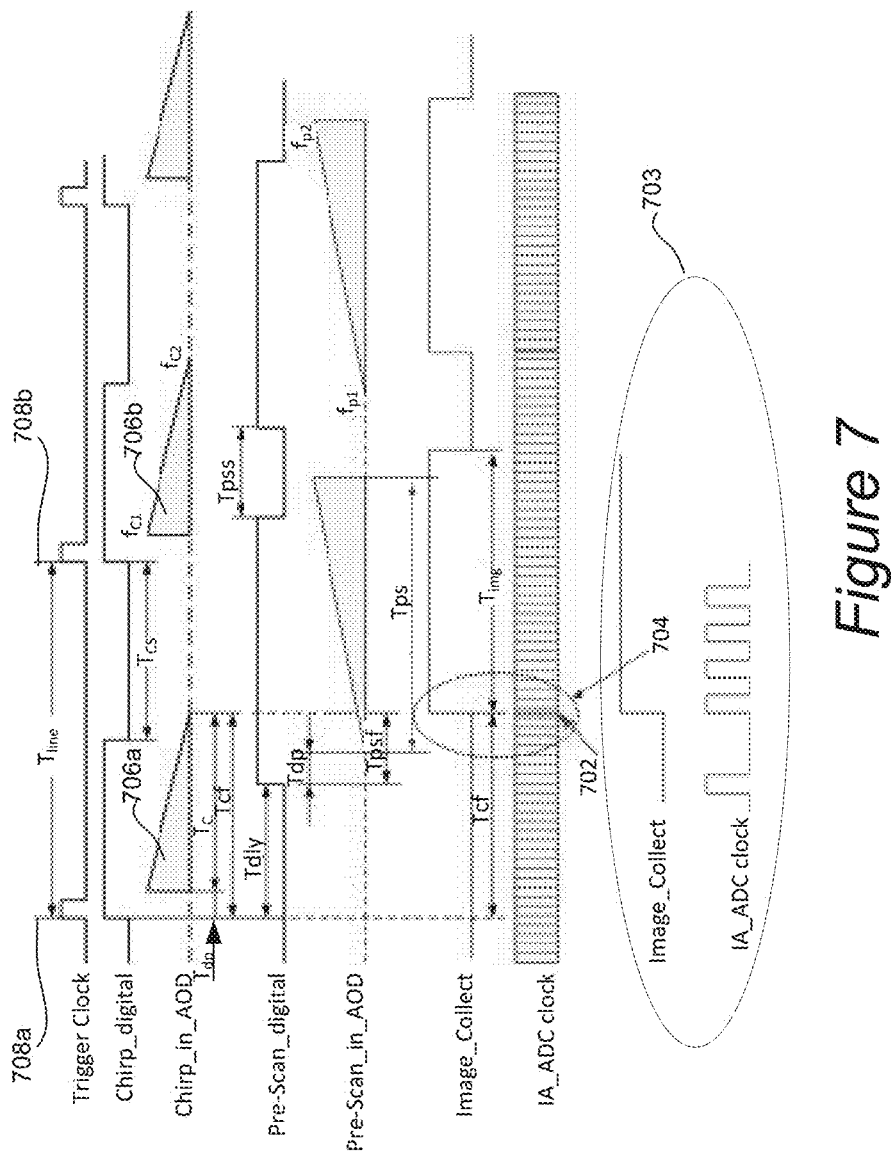
FIG. 7 is a timing diagram illustrating synchronization of scanning and image acquisition timing in accordance with a specific implementation of the present invention.

A digital control module 501 may be configured to receive an external trigger clock and the locally generated system clock Sync_out from the system clock generator 502. The digital control module 501 may also be configured to command the timing sequence for the different AOD and image acquisition clocks (e.g., as shown in FIG. 7) with such timing being synchronized to the local system clock. The synchronization signal clock driver 506 can also be configured to control the timing of the DDS modules and their corresponding scanner and image acquisition channels, for example, by locking the timing of the DDS modules to be in synchronization with respect to each other. The synchronization signal clock driver 506 may receive the system clock (e.g. sync out) and generate independent clocks or triggers (e.g., sync_in) for each DDS module. The synchronization signal clock driver 506 may be formed from any suitable combination of hardware and/or software. For example, synchronization signal clock driver 506 may include one or more FPGA's (field programmable gate arrays), ASIC's (application specific integrated circuits), other logic devices, etc.

Figure 6:
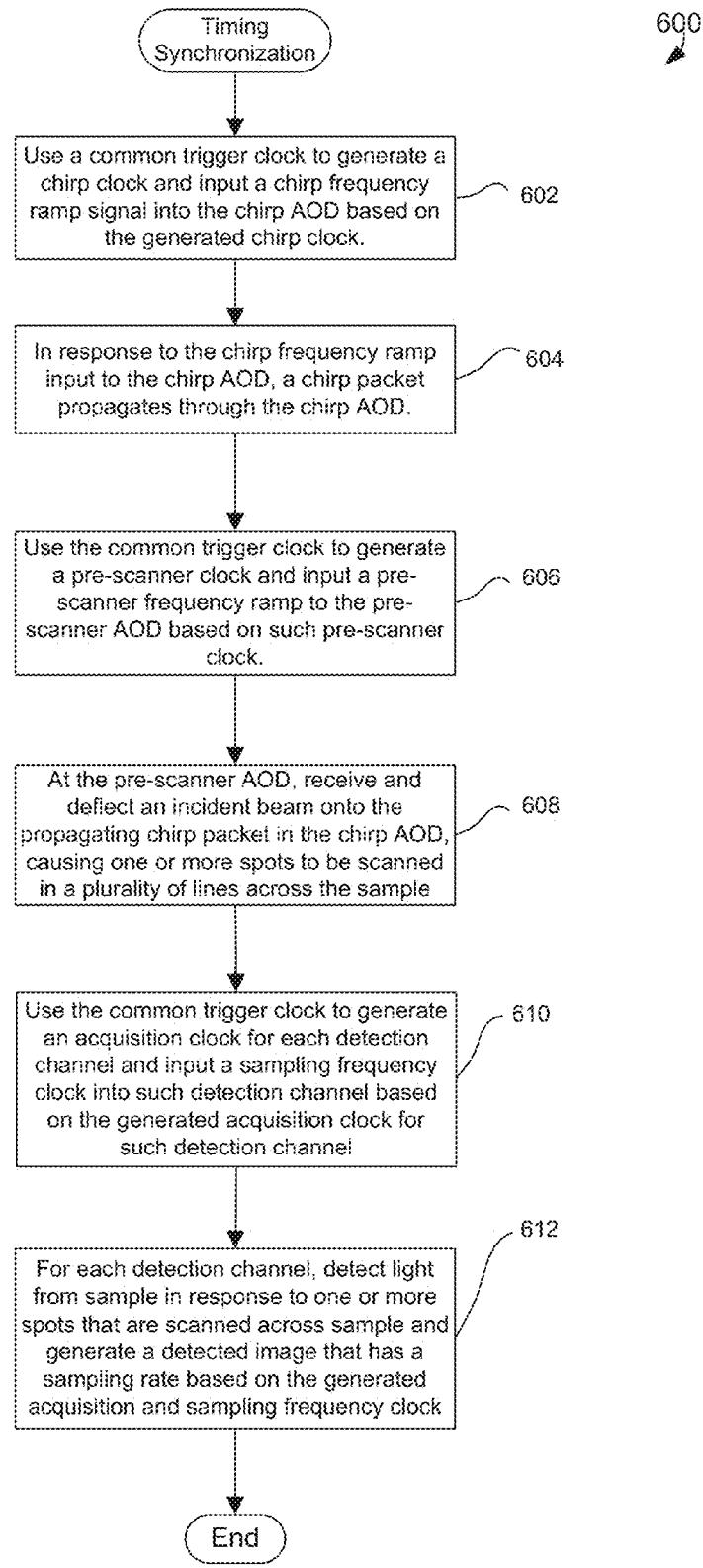
FIG. 6 is a flow chart illustrating a procedure for synchronizing scanning and image acquisition timing in accordance with a specific implementation of the present invention.

Any suitable technique may be utilized to synchronize the scanning and image acquisition timing. FIG. 6 is a flow chart illustrating a procedure 600 for synchronizing scanning and image acquisition timing in accordance with a specific implementation of the present invention. Initially, a common system clock may be used to generate a chirp clock and input a chirp frequency ramp into the chirp AOD (of the inspection tool's scanning system) based on the generated chirp clock in operation 602. In response to the chirp frequency ramp that is input to the chirp AOD, a chirp packet propagates through the chirp AOD in operation 604. This chirp packet has a frequency that depends on the frequency of the chirp frequency ramp, which depends on the frequency of the chirp clock. The timing of both the chirp frequency ramp and the chirp clock depend on the timing of a trigger signal that is based on the system clock.

FIG. 7 is a timing diagram illustrating synchronization of scanning and image acquisition timing in accordance with a specific implementation of the present invention. As shown, a trigger signal (or clock) having period $T_{line}$ is used to generate chirp clock "Chirp_digital". For example, the digital chirp clock has the same period $T_{line}$ as the trigger clock. This digital chirp clock is also used to generate the frequency ramp signal (e.g., Chirp_in_AOD) that is input to the chirp AOD. For instance, a frequency ramp signal is triggered off each rising edge of the digital chirp clock "Chirp_digital" (following a small chirp dead time $T_{dp}$). As shown, a first frequency ramp 706a is triggered by a first edge 708a of the trigger clock, and a second frequency ramp 706b is triggered off the subsequent second edge 708b of the trigger clock. As shown, the frequency input to the chirp AOD ramps down from a first frequency $f_{c1}$ to a second frequency $f_{c2}$. The frequency ramp duration is based on a half cycle (e.g., active high) of the digital chirp clock "Chirp_digital."

The width of an AOD's chirp packet is generally based on the corresponding width of the input frequency ramp. As described herein, the chirp packet focuses beams received from the pre-scanner into a spot onto a scan line, and such spot moves along with the chirp packet as it propagates through the chirp AOD. Since the chirp packet forms a spot and the chirp packet is formed from the chirp frequency ramp, which is based on the trigger clock, the period of the trigger clock is directly related to the chirp packet size and resulting spot size. Accordingly, the trigger clock's period may be selected based on the desired spot size.

The chirp frequency ramp signal may cause chirp packets to propagate one at a time through the chirp AOD so as to cause a spot to scan along a scan line of the specimen. For example, a first frequency ramp (706a) may be input into a first end of a chirp AOD and cause a first chirp packet to propagate from this first end to a second end of the chirp AOD. As the first chirp packet reaches the second end of the chirp AOD, a second frequency ramp (706b) may then cause a second chirp packet to propagate from the first to the second end of the AOD. When each chirp packet reaches the second end, which corresponds to the scan line end, the stage, upon which the specimen is placed, may also be moved relative to the axis of the particular spot so that another line is then scanned in response to the second chirp packet propagation. The trigger clock period may also be selected so that a period of the resulting chirp frequency ramp signal matches the relative stage movement from scan line to scan line. Likewise, the width of the AOD may be selected so that each chirp packet results in a spot being scanned across aligned scan lines. For instance, a first chirp packet results in a spot moving between two x positions of a first scan line (y1), and a second chirp packet results in a spot moving from two x positions of a second scan line (y2) so that each scan line has the same delta x positions.

Referring back to FIG. 6, the trigger clock is also used to generate a pre-scanner clock and input a pre-scanner frequency ramp to the pre-scanner AOD based on such pre-scanner clock in operation 606. The timing of the pre-scanner clock is generally based on the fill time of the chirp AOD and the pre-scanner AOD. As shown in FIG. 7, a pre-scan clock "Pre-Scan_digital" is started after time $T_{dly}$, which is equal to the chirp AOD fill time $T_{cf}$ minus the pre-scanner AOD fill time $T_{psf}$. The pre-scanner frequency ramp "Pre-scan_in_AOD", which is input to the pre-scanner AOD, is triggered off the rising edge of the pre-scanner clock "Pre-Scan_digital" (following a small pre-scanner dead time $T_{dp}$). As shown, the frequency input to the pre-scanner AOD ramps up from a first frequency $f_{p1}$ to a second frequency $f_{p2}$.

At the pre-scanner AOD, an incident beam is received and deflected onto the propagating chirp packet in the chirp AOD, causing one or more spots to be scanned in a plurality of scan lines across the sample in operation 608. For instance, a plurality of spots can be formed from a single scanned spot that is output from the chirp AOD, and these multiple spots are directed to scan onto the sample. Alternatively, multiple deflector systems (e.g., multiple pre-scanner and chirp AOD's) may be used to generate multiple spots on the sample. Regardless of the number of spots per pre-scanner period, multiple scan lines may be scanned by moving the sample stage relative to the scanning spots.

The common trigger clock may also be used to generate an acquisition clock for each detection channel and input a sampling frequency clock (e.g., IA_ADC clock) into such detection channel based on such generated acquisition clock in operation 610. For each detection channel, light is detected from the sample in response to the one or more spots scanned across the sample and a detected signal or image is generated. Each channel may detect light from a particular angle and/or from a particular spot. For each detection channel, light is detected from the sample in response to one or more spots that are scanned across the channel and a detected image (or signal) is generated to have a sampling rate based on the generated acquisition clock and sampling frequency clock in operation 612. The procedure may then end.

As shown in FIG. 7, an image acquisition clock "Image_Collect" may triggered after the chirp fill time delay $T_{cf}$. The image acquisition clock has an image collection region that corresponds to when an image is sampled for the corresponding scan line duration $T_{img}$. A corresponding sampling clock "IA_ADC" is input to the particular detection channel based on the generated image acquisition clock for such particular acquisition clock. As shown, the sampling clock "IA_ADC clock" is triggered off the rising edge 702 of the acquisition clock "Image_Collect." Timing portion 703 is an expanded view of area 704 of the Image_Collect and IA_ADC clock.

Each image acquisition and associated sampling clock may also be adjusted to compensate for optical distortion in the respective channel. For instance, it may first be determined how much distortion in position is present for each scan spot. A reference sample with known structures at known positions may be inspected to obtain a test image. The test image can then be compared to a reference image that is simulated without optical distortion. For instance, the design data for a reference wafer may be used to simulate a reference image of various spots that are produced by ideal optics having no distortion. For each spot, the difference between positions of the test image structures may then be compared with the positions of the reference structures to obtain a distortion amount. Different sampling frequencies can then be applied to the test sample to obtain an optimum frequency for sampling each spot so that the distortion is corrected for such spot. The optimum frequency to correct each spot's distortion may then be stored for later use by the sampling clock generator. For example, the image acquisition clock (and resulting sampling clock) for each spot may then be adjusted by a frequency amount that is selected to correct the distortion for such spot.

Figure 8:
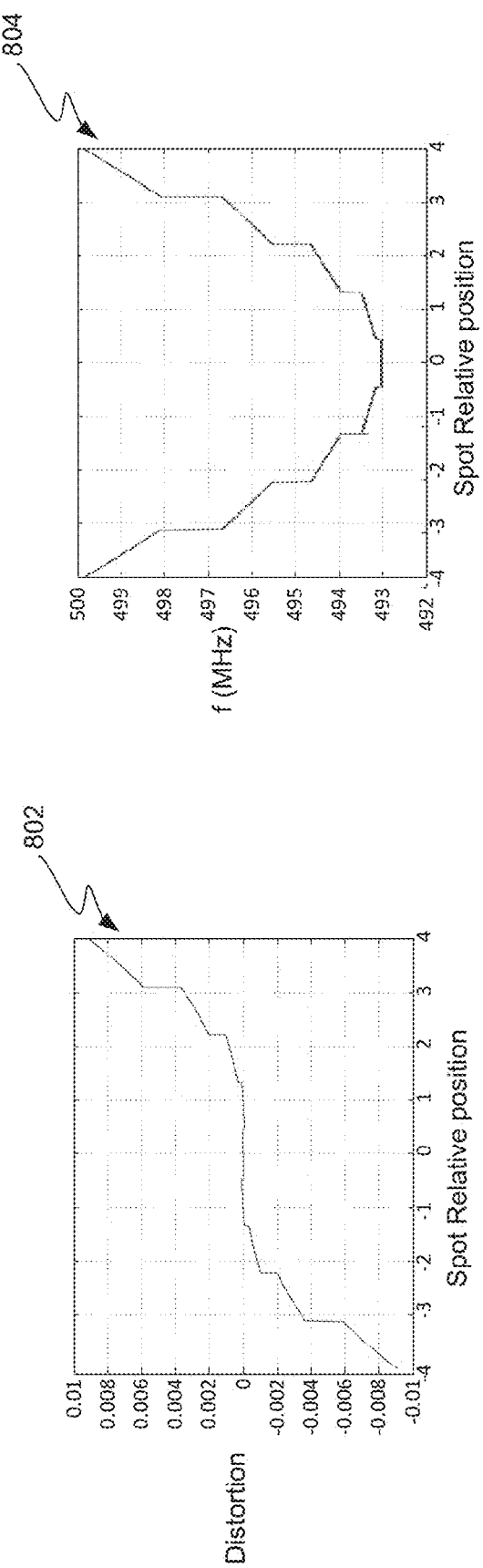
FIG. 8 show graphs for position distortion as a function of spot position and image sampling frequency selection as a function of spot position in accordance with one embodiment of the present invention.

FIG. 8 show graphs for position distortion as a function of spot position and image sampling frequency selection as a function of spot position in accordance with one embodiment of the present invention. Graph 802 illustrates distortion as a function of the relative position of 9 spots. Graph 804 illustrates the frequency for correcting the distortion for each relative position of the 9 spots. For instance, the image acquisition clock for the spot at position 1 can be set to about 493.5 MHz, while the acquisition clock for the spot at position 2 may be set at about 494.5 MHz.

In general, controlling the sampling rate controls the locations that are sampled on the sample as each spot is scanned across such sample. The sampled locations can be controlled so that the sampled locations follow the spots as they scan across scan lines of the sample. Additionally, the sampling of each spot can be adjusted so that the sampled location precisely follows such spot as it traverses from line to line so as to minimize line jitter. The sampling of each spot can be adjusted so that the scanned location compensates for distortion in optics for such spot (e.g., illumination and/or collection optics).

The detected images (or signals) may then be analyzed to determine whether defects are present on the sample. For example, the intensity values from a target die are compared to the intensity values from a corresponding portion of a reference die (or generated from a design database), where a significant intensity difference may be defined as a defect. These inspection systems may implement any suitable inspection technology, along with the novel image synchronization mechanisms described further below. By way of examples, brightfield and/or darkfield optical inspection mechanisms may be utilized. The mechanisms of the present invention may also be implemented within a scanning electron microscopy system.

Each detected image may also be input to a defect (e.g., image) processor (e.g., 101). Defect processor may include mechanisms for processing the received data, such as buffering, compressing, packing, filtering noise, generating images based on the input signal, analyzing images to detect defects on the sample, etc. The majority of defects may be found by detecting contrast, defined as the ratio of the intensities in the target and reference dies, rather than by threshold, which is defined as the difference between the intensities.

The inspection techniques described herein may be implemented on various specially configured inspection or metrology systems, such as the one schematically illustrated in FIG. 1. In certain embodiments, a system for inspecting or measuring a specimen includes various controller components for implementing the techniques described herein. The controller may be implemented by any suitable combination of hardware and/or software, such as a processor, memory, programmable device or field programmable gate array (FPGA), etc.

The inspection system may be associated with a computer system that is configured (e.g., with programming instructions) to provide a user interface (e.g., on a computer screen) for displaying resultant inspection characteristics. The computer system may also include one or more input devices (e.g., a keyboard, mouse, joystick) for providing user input, such as changing detection parameters. In certain embodiments, the computer system is configured to carry out inspection techniques in conjunction with other inspection components, such as controller 101, detailed herein. The computer system typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting or measuring a specimen using an inspection system comprising a beam generator module and a plurality of detection channels, the method comprising:
   using a common trigger clock to generate one or more deflectors clocks that are input to the beam generator module that receives and deflects an incident beam so as to cause one or more spots to be scanned in a plurality of lines across the specimen;
   using the common trigger clock to generate an acquisition clock for each detection channel and input a sampling frequency signal into such detection channel based on the generated acquisition clock for such detection channel; and
   at each detection channel, detecting light from the specimen in response to the one or more spots scanned across the specimen and generating a detected image that has a sampling rate that is based on the sampling frequency signal.

2. The method of claim 1, wherein at least one of the one or more deflector clocks has a same period as the common trigger clock.

3. The method of claim 1, wherein a period of the common trigger clock is selected based on a desired size of each spot.

4. The method of claim 1, wherein the beam generator module comprises a pre-scanner acousto-optic deflector (AOD) and a chirp AOD, wherein the one or more deflector clocks include a chirp clock for inputting a chirp frequency ramp signal into the chirp AOI, wherein the one or more deflector clocks further include a pre-scanner clock for inputting a pre-scanner frequency ramp signal into the pre-scanner AOI, wherein a period of the common trigger clock is selected so that a period of the resulting chirp frequency ramp signal matches a relative stage movement that causes scanning of the one or more spots to move from a first set of one or more scan lines to a second set of one or more scan lines.

5. The method of claim 4, wherein the pre-scanner clock is delayed from the chirp clock by a time duration equal to a fill time of a chirp AOD propagating through the chirp AOD minus a fill time of the pre-scanner AOD.

6. The method of claim 4, wherein the inspection system further comprises a diffractive element or mirror system for receiving a single spot deflected from the chirp AOD and causing a plurality of spots to be scanned in a plurality of lines across the specimen.

7. The method of claim 1, wherein the acquisition clock and associated sampling frequency signal for each detection channel is controlled so that sampling a plurality of locations on the specimen substantially accurately follows the scanning of the one or more spots as they traverse along the plurality of lines.

8. The method of claim 1, wherein the acquisition clock and associated sampling frequency signal for each spot of each detection channel is controlled so that sampling a plurality of locations on the specimen follows the scanning of such spot at it scans along a plurality of lines.

9. An system for inspecting or measuring a specimen, comprising:
   a beam generator module for scanning one or more incident spots across a plurality of scan portions of the specimen, wherein the scan portions include one or more first scan portions and one or more next scan portions that are scanned after the one or more first scan portions;
   one or more detection channels for sensing light emanating from the specimen in response to the one or more incident spots scanned across the scan portions and generating a detected image for each scan portion as an incident beam is scanned over such scan portions; and
   a synchronization system comprising a plurality of clock generator modules for receiving a common clock and generating one or more deflectors clocks that are input to the beam generator module so as to cause the one or more spots to be scanned across the scan portions and generating an acquisition clock for inputting a sampling frequency signal into each detection channel based on the generated one or more deflector clocks to generate a detected image at a synchronized timing so as to minimize jitter between the scan portions in the detected image, wherein the one or more deflector clocks and the acquisition clock are generated based on the common system clock.

10. The system of claim 9, wherein the clock generator modules comprise a plurality of direct digital synthesizers (DDS's) for generating a scanning clock for the beam generator module and generating a sampling rate for each detection channel, wherein the synchronization system further comprises a synchronization signal clock driver for determining a timing for each DDS module.

11. The system of claim 9, wherein the beam generator module comprises a pre-scanner AOD and a chirp AOD and wherein the synchronization system is configured to perform the following operations:
using the common trigger clock to generate a chirp clock and input a chirp frequency ramp signal into the chirp AOD based on the generated chirp clock;
in response to the chirp frequency ramp signal input to the chirp AOD, propagating a chirp packet through the chirp AOD;
using the common trigger clock to generate a pre-scanner clock and input a pre-scanner frequency ramp signal into the pre-scanner AOD based on the generated pre-scanner clock, wherein the pre-scanner AOD receives and deflects an incident beam onto the propagating chirp packet in the chirp AOD, causing the one or more incident spots to be scanned in a plurality of lines across the specimen;
using the common trigger clock to generate the acquisition clock for each detection channel and input a sampling frequency signal into such detection channel based on the generated acquisition clock for such detection channel; and
at each detection channel, causing light to be detected from the specimen in response to the one or more incident spots scanned across the specimen and causing a detected image to be generated that has a sampling rate based on the sampling frequency signal.

12. The system of claim 11, wherein the chirp clock has a same period as the common trigger clock.

13. The system of claim 12, wherein the chirp frequency ramp signal is triggered off an edge of the chirp clock.

14. The system of claim 12, wherein the chirp frequency ramp signal has a period that is equal to half a period of the chirp clock and the common trigger clock.

15. The system of claim 11, wherein a period of the common trigger clock is selected based on a desired size of each spot.

16. The system of claim 11, wherein a period of the common trigger clock is selected so that a period of the resulting chirp frequency ramp signal matches a relative stage movement that causes scanning of the one or more incident spots to move from a first set of one or more scan lines to a second set of one or more scan lines.

17. The system of claim 11, wherein the pre-scanner clock is delayed from the chirp clock by a time duration equal to a fill time of the chirp AOD minus a fill time of the pre-scanner AOD.

18. The system of claim 11, further comprises a diffractive element or mirror system for receiving a single spot deflected from the chirp AOD and causing a plurality of spots to be scanned in a plurality of lines across the specimen.

19. The system of claim 11, wherein each image acquisition clock of each detection channel is triggered after a fill time of the chirp AOD.

20. The system of claim 9, wherein a frequency of each acquisition clock is adjusted based on a predefined distortion amount of the corresponding detection channel.

21. The system of claim 9, wherein a frequency of each acquisition clock is adjusted per each spot of the corresponding detection channel, wherein such adjustment is based on a predefined distortion amount for such spot.

22. The system of claim 9, wherein the acquisition clock and associated sampling frequency signal for each detection channel is controlled so that sampling a plurality of locations on the specimen substantially accurately follows the scanning of the one or more incident spots as they traverse along the plurality of lines.

23. The system of claim 9, wherein the acquisition clock and associated sampling frequency signal for each spot of each detection channel is controlled so that sampling a plurality of locations on the specimen follows the scanning of such spot at it scans along a plurality of lines.

* * * * *